United States Patent
Thommen

(10) Patent No.: US 8,216,178 B2
(45) Date of Patent: Jul. 10, 2012

(54) BREAST PUMP SET

(75) Inventor: Daniel Thommen, Steinhausen (CH)

(73) Assignee: Medela Holding AG, Baar (CH)

(*) Notice: Subject to any disclaimer, the term of this patent is extended or adjusted under 35 U.S.C. 154(b) by 470 days.

(21) Appl. No.: 11/793,580

(22) PCT Filed: Dec. 7, 2005

(86) PCT No.: PCT/CH2005/000730
§ 371 (c)(1),
(2), (4) Date: Jun. 20, 2007

(87) PCT Pub. No.: WO2006/079229
PCT Pub. Date: Aug. 3, 2006

(65) Prior Publication Data
US 2008/0021380 A1    Jan. 24, 2008

(30) Foreign Application Priority Data
Jan. 28, 2005    (CH) .................................. 0140/05

(51) Int. Cl.
*A61M 1/06* (2006.01)
*A61J 9/00* (2006.01)
*A61J 11/00* (2006.01)
*A41C 3/04* (2006.01)

(52) U.S. Cl. .............. 604/74; 215/11.1; 450/36; 604/73

(58) Field of Classification Search ............... 604/74
See application file for complete search history.

(56) References Cited

U.S. PATENT DOCUMENTS

| 5,542,921 | A | 8/1996 | Meyers et al. |
| 5,687,717 | A | * 11/1997 | Halpern et al. ............... 600/300 |
| 6,004,288 | A | * 12/1999 | Hochstedler et al. ........... 604/74 |
| 6,517,513 | B1 | * 2/2003 | Covington et al. ............. 604/74 |
| 6,673,036 | B1 | 1/2004 | Britto |
| 7,223,255 | B2 | * 5/2007 | Myers et al. .................... 604/74 |
| 2003/0040734 | A1 | * 2/2003 | Morton et al. ................. 604/514 |
| 2003/0066534 | A1 | 4/2003 | Spetzler et al. |
| 2005/0020971 | A1 | 1/2005 | McKendry et al. |
| 2005/0059928 | A1 | * 3/2005 | Larsson ......................... 604/74 |
| 2008/0045887 | A1 | * 2/2008 | Larsson et al. ................. 604/74 |

FOREIGN PATENT DOCUMENTS

| CN | 1298173 | A | 6/2001 |
| CN | 2555029 | Y | 6/2003 |
| DE | 20319642 | U1 | 3/2004 |
| JP | S6180216 | A1 | 4/1986 |
| JP | 2003220077 | A | 8/2003 |
| JP | 2003235960 | A | 8/2003 |
| JP | 3102400 | U | 3/2004 |

* cited by examiner

Primary Examiner — Christopher D Koharski
Assistant Examiner — Ian Holloway
(74) Attorney, Agent, or Firm — McDonnell Boehnen Hulbert & Berghoff LLP

(57) ABSTRACT

A breast pump set for expressing human breastmilk comprises a breastshield (1) to be placed on the female breast with a coupling part (12) for connection to a milk collection container (2), and an electrically driven suction pump (4, 4'). The breastshield (1) is provided with an actuator (5) for actuating the suction pump. The inventive breast pump seat allows easy handling of the suction pump and eliminates the need for the mother to have a hand free for handling.

18 Claims, 6 Drawing Sheets

BREAST PUMP SET

CROSS-REFERENCE TO RELATED APPLICATIONS:

This application is a U.S. National Phase Application pursuant to 35 U.S.C. §371 of International Application No. PCT/CH2005/000730 filed Dec. 7, 2005, which claims priority to Swiss Patent Application No. 00140/05 filed on Jan. 28, 2005. The entire disclosure content of these applications are herewith incorporated by reference into the present application.

TECHNICAL FIELD

The invention relates to a breastpump set, a breastshield and a connecting tube.

PRIOR ART

Breastpumps for expressing human breastmilk are well known. There are basically two different types. The first are operated manually, i.e. the vacuum needed for milk expression is generated by manual actuation of the suction pump. In the second type, the suction pump is driven electrically, in which case the suction pump can be connected to the mains electricity and/or can be operated by a battery or another energy storage means.

To ensure that the function of the breastpump can be adapted optimally to the needs of the mother, some of the pumps allow the mother to regulate the vacuum. For example, US 2004/0024351 and U.S. Pat. No. 4,813,932 disclose manually actuated breastpumps that have adjustable valves. In the case of manually operated pumps, the suction capacity of the pump itself is additionally regulated by means of the mother increasing or decreasing the pump strength to meet her requirements.

In electrically driven pumps too, it is customary for air release means to be arranged on the breastshield or on the connecting line to the suction pump. This is the case in U.S. Pat. Nos. 6,706,012 and 6,042,560, for example.

U.S. Pat. No. 6,110,140 proposes a manually or electrically operated breastpump which, in the area of the breastshield, has a vacuum regulator for regulating the vacuum generated by the suction pump. This regulator can be actuated during use of the breastpump, such that the vacuum prevailing in the breastshield can be adjusted.

In addition to the solutions described above, which all allow the vacuum generated by the suction pump to be modified in the area of the breastshield, some electrically driven breastpumps also afford the possibility of modifying the vacuum or the suction rhythm on the pump unit itself. This is done via corresponding actuation switches or buttons that are arranged on the suction pump. However, to be able to actuate these buttons, the mother has to have one hand free. This is not possible, however, especially if the mother wishes to express milk from both breasts simultaneously.

SUMMARY OF THE INVENTION

It is therefore an object of the invention to allow the mother to operate the suction pump as easily as possible.

This object is achieved by a breastpump set, a breastshield and a connecting tube.

The breastpump set according to the invention for expressing human breastmilk comprises a breastshield to be placed on a mother's breast, a milk collection container, and an electrically driven suction pump, in which the breastshield has an operating means for operating the suction pump.

By virtue of the breastpump set according to the invention, the mother is therefore able to influence the function of the suction pump without having to be able to reach the latter. The mother can use the same hand with which she is holding the breastshield to her breast. She can therefore express milk from both breasts simultaneously or use the free hand for something else.

The operating means is preferably arranged nearby on the breastshield funnel.

In preferred embodiments, the operating means is arranged facing upward or sideways in the position of use of the breastshield, to ensure that said operating means is easily accessible. However, depending on the shape and configuration of the breastshield, other locations are also possible for the placement of the operating means, preference being given to locations that are easily accessible and correspond to the natural position adopted by the mother as she expresses milk. Moreover, the operating means can also be arranged on a part of the breastshield that can be folded open, plugged on or removed, with the result that the operating means is exposed only when the mother wishes to use it.

Depending on the embodiment, the suction pump can be switched on and off by the operating means. In addition, or as an alternative to this, its pumping capacity can also be modified according to the requirements of the mother.

If a suction pump is used that can operate two breastshields simultaneously, then, depending on the design of the suction pump, only one of the breastshields is provided with the operating means, and the suction pump operates both breastshields in accordance with the same operating signals. If the suction pump is able to operate the two breastshields with different suction rhythms or pumping capacities, both breastshields can be provided with an operating means in order to individually adjust the suction pump.

The signals can be sent from the operating means to the suction pump mechanically, by wireless transmission, or via corresponding cable connections. In the case of wireless transmission, it is possible, for example, to use a radio antenna, an infrared interface, a Bluetooth signal transmission, or another of the known types of wireless transmission. The cable connection is preferably effected via an electrical signal in a known manner.

Instead of an operating means, it is also possible to use a voice recognition means, which then transmits a control signal to the suction pump. This voice recognition means can be arranged in the area of the breastshield, directly on the suction pump, or on an additional external unit connected to the suction pump.

The breastshield preferably comprises a main body formed by one piece, in which the operating means and any connecting cables for signal transmission are arranged. To keep the costs of such breastshields as low as possible, however, the main body can also be formed of several pieces, in which case, for example, a breastshield funnel is designed as a disposable product and at least the part with the operating means is able to be reused.

Further advantageous embodiments are set forth in the dependent patent claims.

BRIEF DESCRIPTION OF THE DRAWINGS

The subject matter of the invention is explained below on the basis of preferred illustrative embodiments depicted in the attached drawings, in which.

EMBODIMENTS OF THE INVENTION

Figure 1:
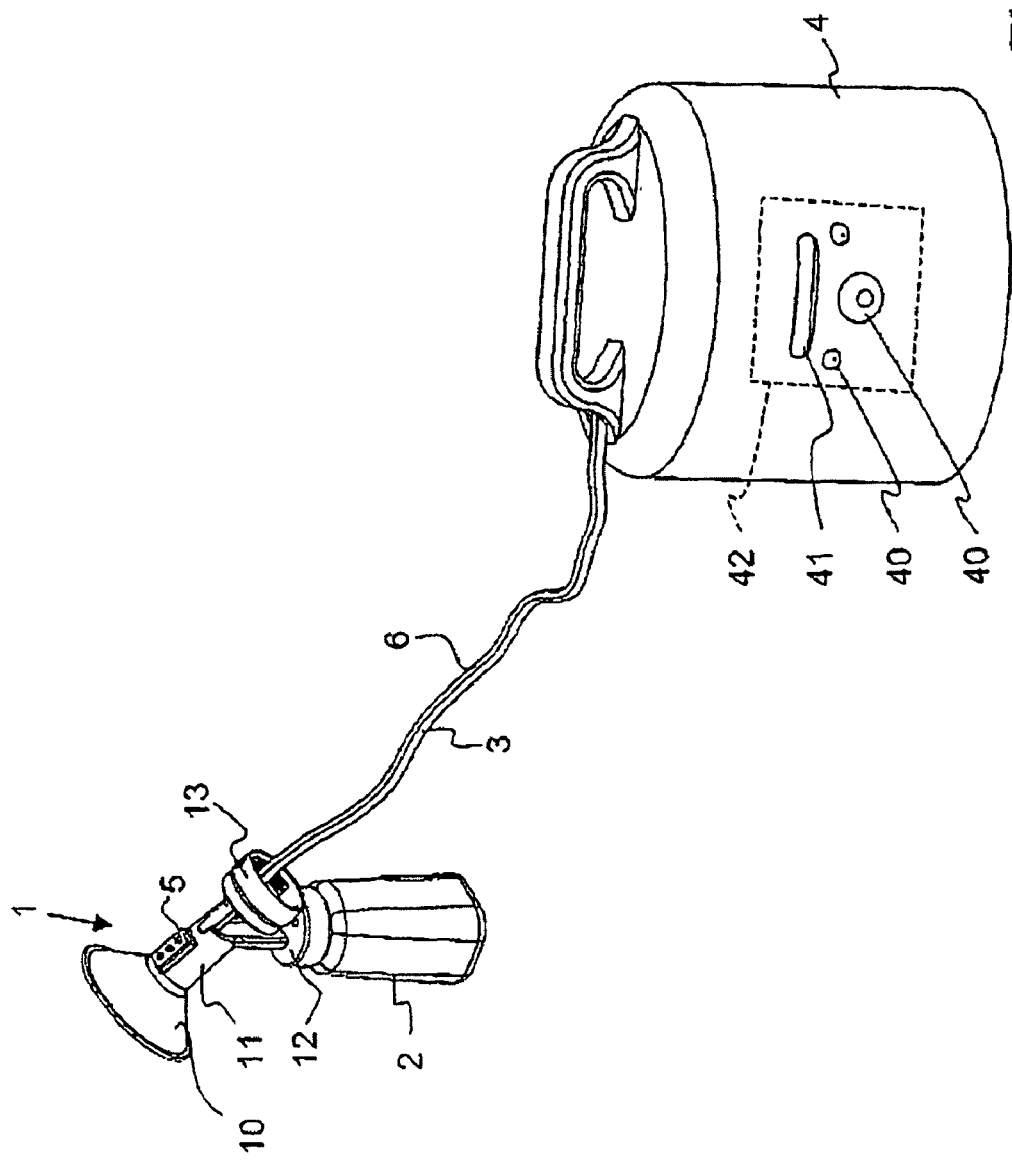
FIG. 1 shows a view of a breastpump set according to a first embodiment of the invention.

FIG. 1 shows a first embodiment of the breastpump set according to the invention. It basically comprises at least one breastshield 1, a milk collection container 2 that can be secured on the breastshield 1, and an electrically driven suction pump 4, which is connected to the breastshield 1 via a suction line 3.

The breastshield 1 has a breastshield funnel 10, which is placed on the mother's breast during use. The funnel 10 merges into a breastshield neck 11, which is adjoined by first and second breastshield coupling parts 12, 13. The first breastshield coupling part 12 has an inner thread that can be screwed onto an outer thread of the milk collection container 2, here a baby's bottle. The second breastshield coupling part 13 has an attachment (not visible in the figure) into which the suction line 3, here a tube, can be fitted.

The other end of the tube can be fitted in the suction pump 4. The vacuum or underpressure generated in the suction pump is applied by way of this tube to the breastshield, such that the milk is expressed from the mother's breast and can be collected in the milk collection container 2.

FIG. 1 shows the customary position of use. The first coupling part 12 is directed downward, and the second coupling part 13 is directed rearward or obliquely downward, in any case away from the mother's breast.

The suction pump 4 can be one of the known motor-driven suction pumps. It preferably has actuating and control keys or buttons 40 and a display 41. In the illustrative embodiment shown here, it is designed as an independent, portable unit.

According to the invention, the breastshield 1 now has an operating means, here in the form of an operating panel 5, via which the suction pump 4 can be operated. This operation is preferably performed independently of the setting of the actuating and control keys or buttons 40 arranged on the suction pump 4.

The operation can involve the switching on and off of the suction pump 4, but also the adjustment of the suction rhythm, the suction curve, the suction capacity, the intervals between individual cycles, etc.

The operating panel 5 is preferably arranged in the area of the breastshield funnel 10. In the example shown here, it is secured on or fitted into the breastshield neck 11 adjacent to the funnel 10. It is preferably directed upward in the position of use shown here, such that it can be reached by the same hand with which the mother is holding the breastshield 1 to her breast. However, the operating panel 5 can also be arranged on the side or bottom of the neck 11, for example.

The operating panel 5 is secured on or in the breastshield 1 by known means. The main body of the breastshield 1 itself is usually made of plastic and is designed in one piece or several pieces. The operating panel 5 can, for example, be cast into this main body or affixed to it by adhesion. In the latter case, the main body can have a suitable recess in which the operating panel 5 can be fitted, such that the latter does not protrude too far and is thus protected. Any cables for signal transmission can be connected in the same way to the breastshield 1 or integrated in it.

The operating panel 5 can comprise switches, push keys, sensor keys, rotatable knobs, slides or other known means, such that the mother can transmit the desired control signals to the suction pump 4 and to the control system 42 arranged therein.

In the illustrative embodiment shown here, the signals are transmitted from the breastshield 1 to the suction pump 4 via a signal line 6. This line can run separate from the suction line 3 and can also be connected via other attachment points to the breastshield 1 and to the suction pump 4. However, a connecting tube is preferably used that contains both the suction line 3 and also the signal line 6. Depending on the design, there can be more than one suction line 3 and more than one signal line 6. The at least two lines 3, 6 are preferably connected to one another along their entire length. For example, they are co-extruded or, after being produced separately, are encapsulated together. At both ends, they have plugs that can be fitted into corresponding sockets in the breastshield 1 and the suction pump 4.

If two breastshields 1 are attached to the same suction pump 4, there are of course two connecting tubes with suction lines 3, in which case both tubes or only one of them can additionally have a signal line 6.

Figure 2:
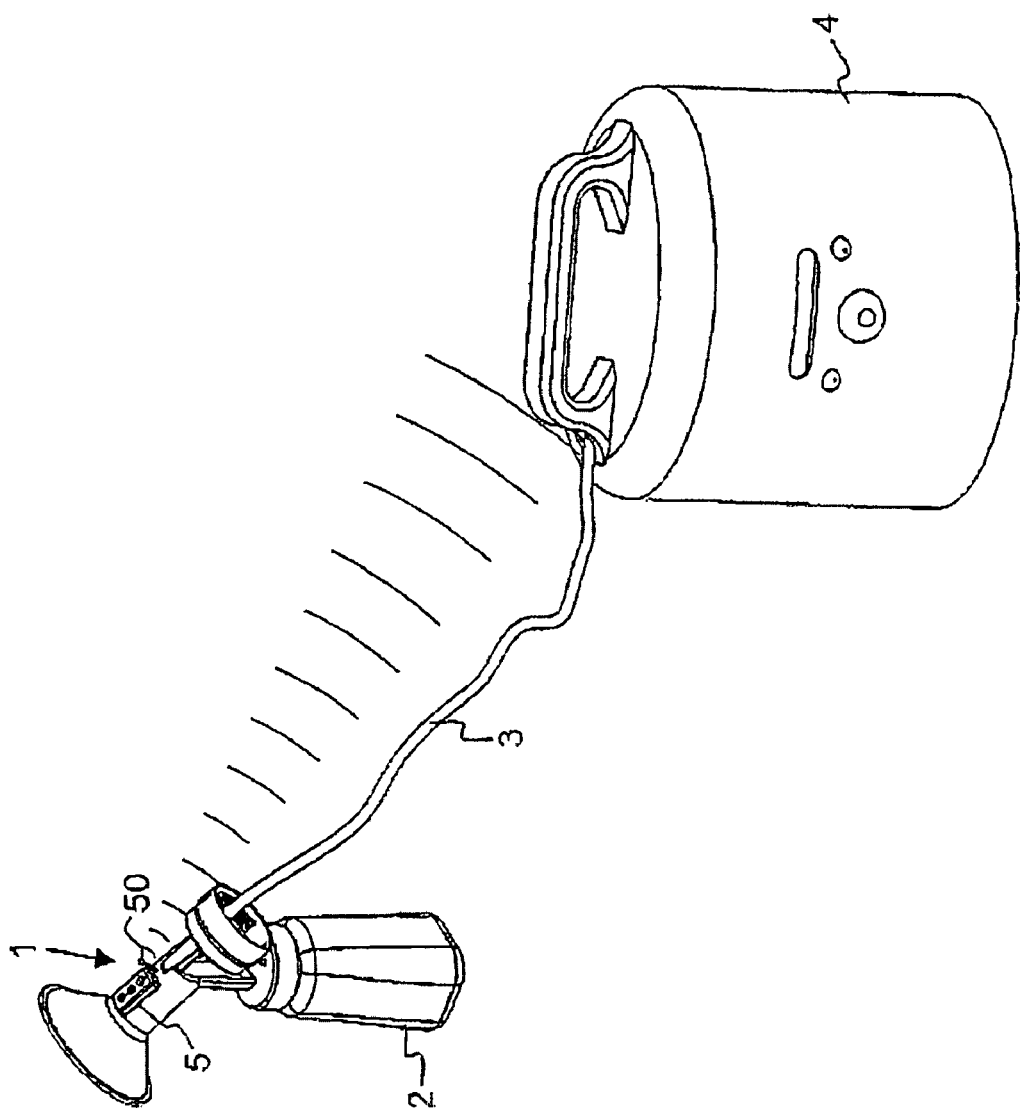
FIG. 2 shows a view of a breastpump set according to a second embodiment of the invention.

An alternative embodiment is shown in FIG. 2. Identical parts have been provided with the same reference numbers. Here, the signals are not sent from the breastshield 1 to the suction pump 4 via a line, but instead by wireless transmission, preferably by radio. An antenna 50 is shown here as one representative of all the possibilities of wireless transmission, and it will be noted that the presently available antennas can generally be integrated into the breast shield 1 in a planar manner.

Figure 3:
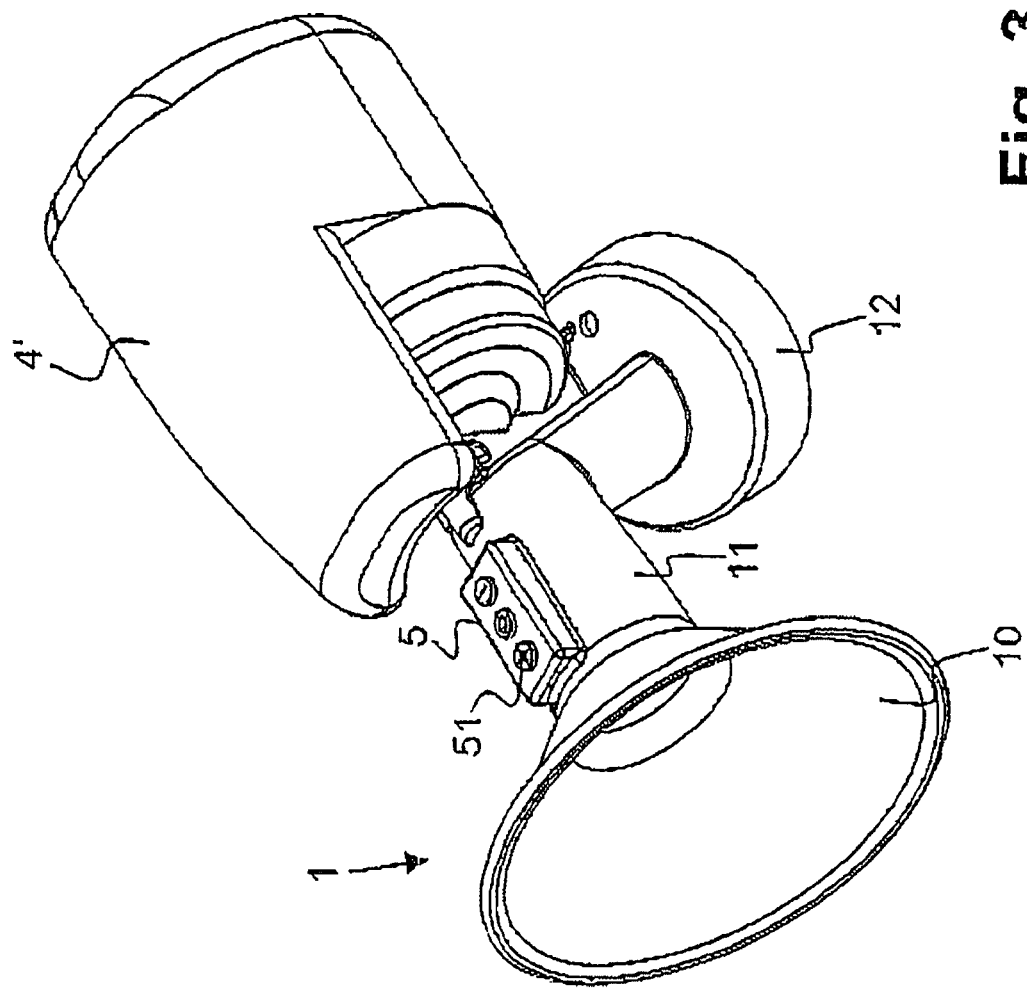
FIG. 3 shows a view of a breastpump set according to a third embodiment of the invention.
Figure 4:
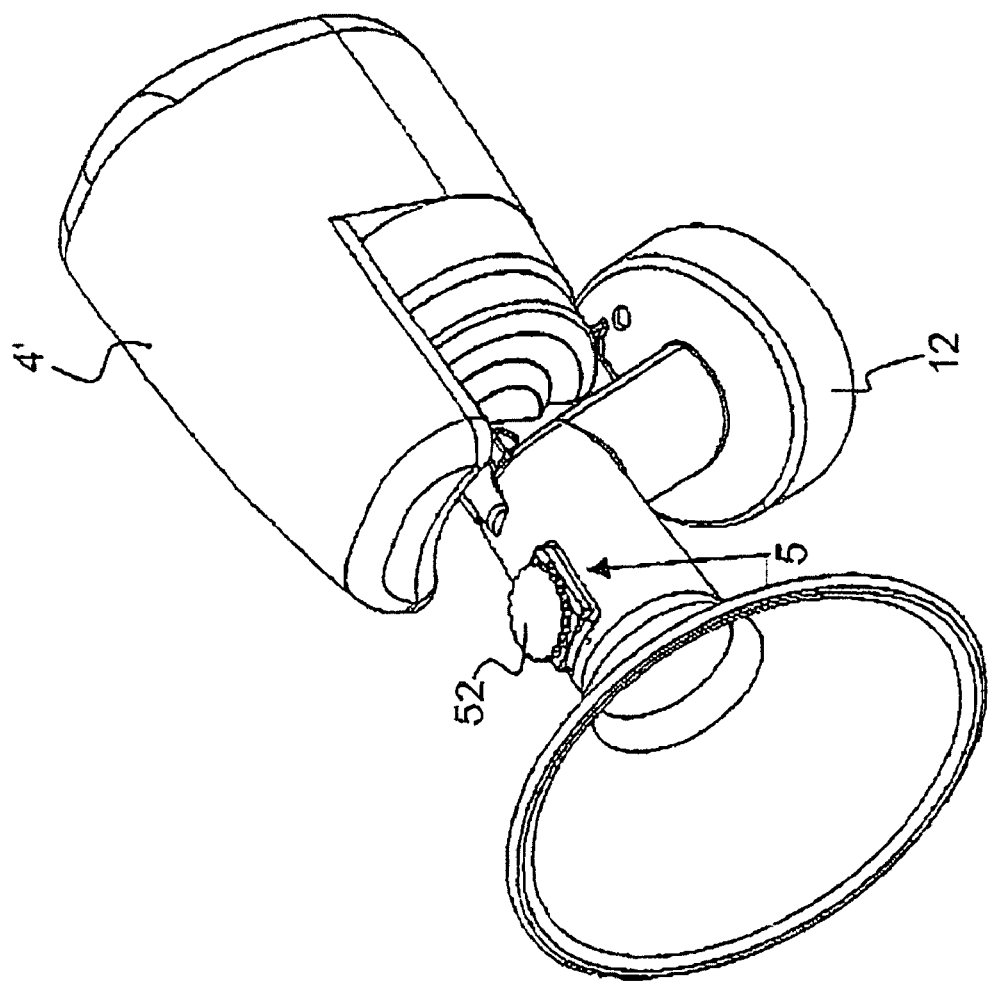
FIG. 4 shows a view of a breastpump set according to a fourth embodiment of the invention.

In the illustrative embodiments according to FIGS. 3 and 4, the milk collection container 2 is not shown. It is, however, screwed onto the first coupling part 12 in the known manner. In contrast to the above embodiments, the suction pump is in this case a suction pump unit 4' that is secured directly on the second coupling part 13 of the breastshield 1. Such suction pumps usually have a battery or another energy storage means, which is likewise arranged in this unit 4'. The suction pump unit 4' is secured on the breastshield 1 in a known manner, for example by a screw connection, clamping means, or another form-fit or force-fit securing means.

To ensure that it can be easily reached by the fingers, the operating panel 5 of the pump 4' is not arranged on the unit itself, but instead on the breastshield 1, preferably in the area of the funnel 10 as before. In this case too, the neck 11 of the shield 1 has proven to be a particularly suitable location.

In FIG. 3, the operating panel 5 has at least one, preferably several keys 51, and in FIG. 4 it has at least one rotatable knob 52.

Figure 5:
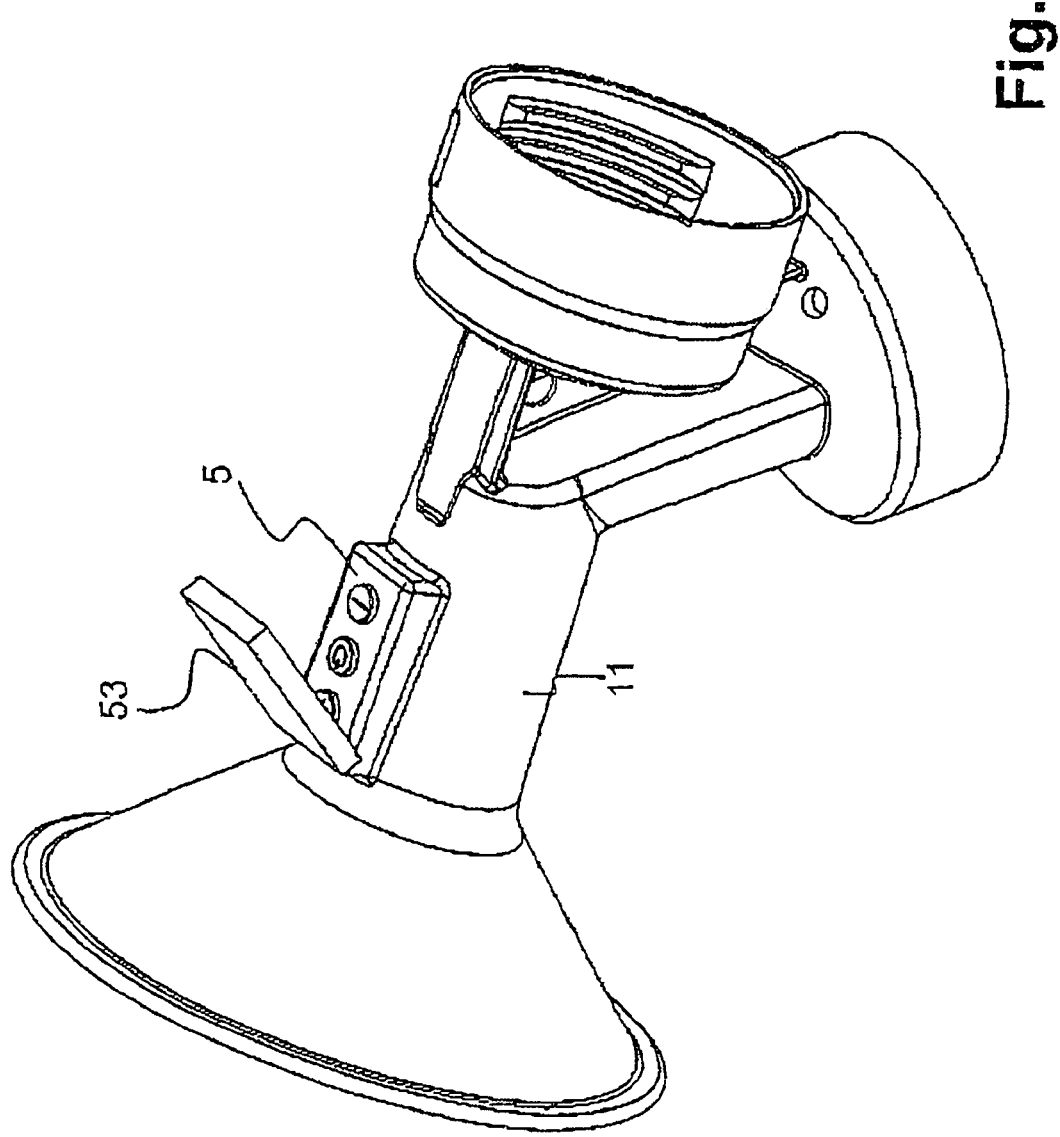
FIG. 5 shows a view of a breastshield according to a fifth embodiment.
Figure 6:
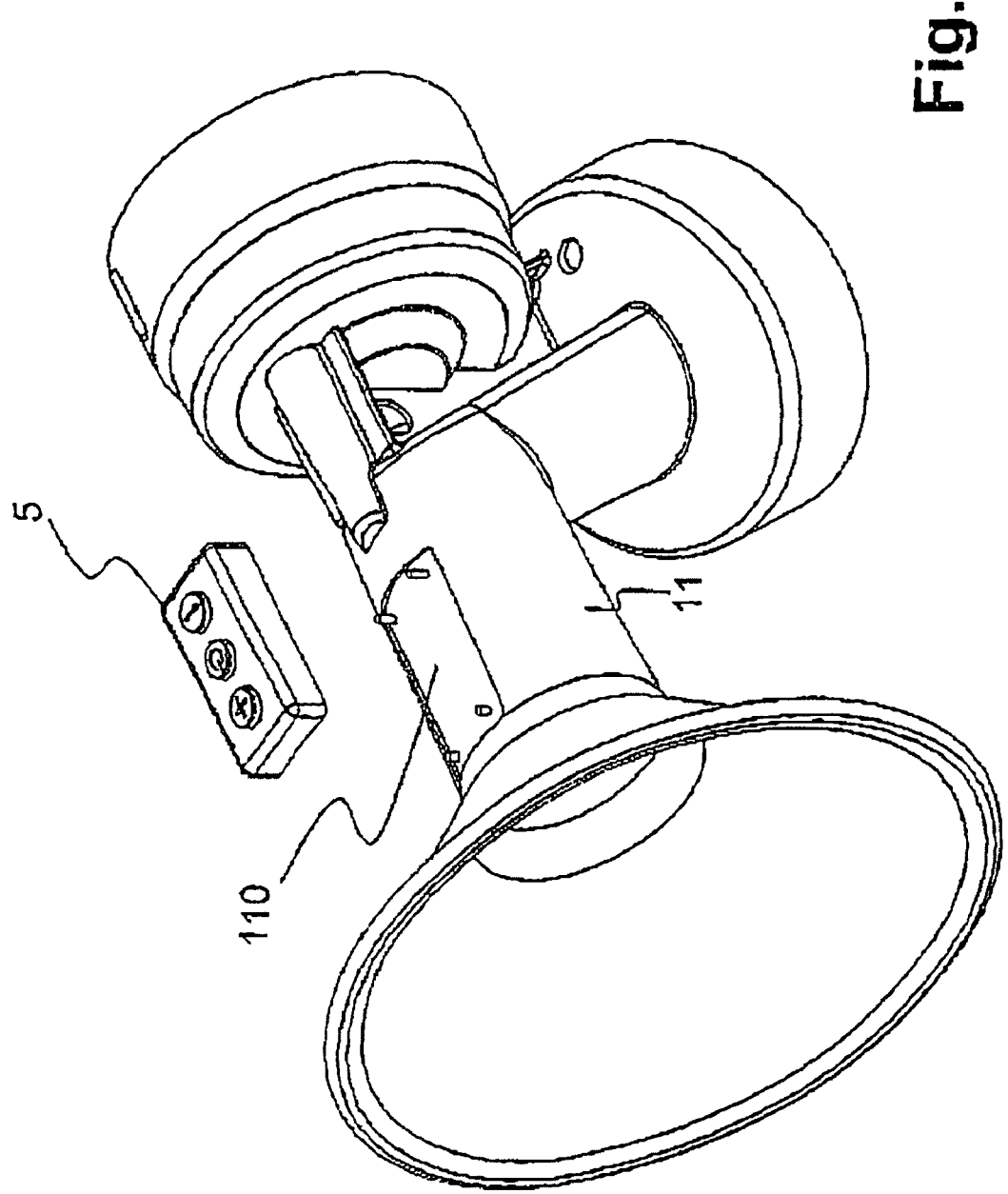
FIG. 6 shows a view of a breastshield according to a sixth embodiment.

In the embodiment according to FIG. 5, the operating panel 5 is protected by a flap 53 that can be folded open. In FIG. 6, the operating panel 5 can be plugged on, in which case the breastshield neck 11 has a corresponding recess 100 with pins that engage in securing holes of the panel 5.

The signals can again be sent to the suction pump unit 4' via signal lines or by wireless transmission. If signal lines are used, the contact or connection between the line sections routed in the breastshield 1 and in the suction pump unit 4' is preferably made automatically when the pump 4' is coupled to the shield 1.

The breastpump set according to the invention thus permits easy operation of the suction pump and eliminates the need for the mother to have one hand free for handling it.

The invention claimed is:
1. The breastpump set comprises a breastshield with a coupling part for connection to a milk collection container, and an electrically driven suction pump, the suction pump located external to the breastshield, wherein the breastshield has an operating panel for operating the suction pump panel comprising at least one of the following: a switch, a push key, a sensor key, rotatable knob, and a slide.
2. The breastpump set as claimed in claim 1, in which it further comprises a suction line for connecting the suction pump to the breastshield.
3. The breastpump set as claimed in claim 1, in which the suction pump is secured on the breastshield.
4. The breastpump set as claimed in claim 1, in which the operating panel is connected via a signal line to a control system arranged in the suction pump.
5. The breastpump set as claimed in claim 2 or 4, in which the signal line is connected to the suction line.
6. The breastpump set as claimed in claim 1, in which the operating panel wirelessly transmits signals to the suction pump.
7. The breastpump set as claimed in claim 1, in which it comprises two breastshields, and in which the suction pump is equipped for simultaneous suctioning of two breasts.
8. A breastshield for use in a breastpump ~et, in which the breastshield has a breastshield funnel, a first coupling part for connection to a milk collection container, and a second coupling part for connection to a suction pump, the suction pump located external to the breastshield, wherein the breastshield has an operating panel for operating the suction pump panel comprising at least one of the following: a switch, a push key, a sensor key, rotatable knob, and a slide.
9. The breastshield as claimed in claim 8, in which the second coupling part can be connected to the suction pump via a suction line.
10. The breastshield as claimed in claim 8, In which the second coupling part is secured to the suction pump.
11. The breastshield as claimed in claim 8, in which the operating panel is arranged in the area of the breastshield funnel.
12. The breastshield as claimed in claim 11, in which the operating panel is arranged on a breastshield neck adjoining the breastshield.
13. The breastshield as claimed in claim 11, in which, in the position of use, the first coupling part is directed downward and the operating panel is arranged on an upwardly directed or downwardly directed or laterally directed area of the breastshield.
14. The breastshield as claimed in claim 8, in which the breastshield has a part which can be plugged on, opened or removed and on which the operating panel is arranged.
15. The breastpump of claim 1, further comprising a connecting tube for use in a breastpump set, wherein the connecting tube has at least one suction line and at least one signal line.
16. The breastpump as claimed in claim 15, in which the suction line and the signal line are connected to one another along their entire length.
17. A breastpump set for expressing human breastmilk, in which the breastpump set comprises a breastshield with a coupling part for connection to a milk collection container, and an electrically driven suction pump, wherein the suction pump can be operated by a voice recognition system.
18. The breastpump as claimed in claim 17, in which the voice recognition system is arranged in the area of the breastshield or on the suction pump or on an additional external unit connected to the auction pump.

* * * * *